(12) United States Patent
Camenzind et al.

(10) Patent No.: US 6,255,259 B1
(45) Date of Patent: Jul. 3, 2001

(54) PHOSPHORUS-FREE MULTIFUNCTIONAL ADDITIVES FOR LUBRICANTS

(75) Inventors: Hugo Camenzind, Bern; Alfred Dratva, Bottmingen; Peter Hänggi, Giffers, all of (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/503,018

(22) Filed: Feb. 11, 2000

(30) Foreign Application Priority Data

Jul. 30, 1997 (CH) .................................................. 1823/97

(51) Int. Cl.⁷ ................................................ C07D 285/12
(52) U.S. Cl. ........................................... 508/271; 548/142
(58) Field of Search .............................. 548/142; 508/271

(56) References Cited

U.S. PATENT DOCUMENTS

| | | | |
|---|---|---|---|
| 2,323,037 | 6/1943 | Harman et al. | 260/787 |
| 3,291,841 | 12/1966 | O'Shea | 260/611 |
| 4,652,653 | 3/1987 | Baumann et al. | 548/171 |
| 4,818,777 | 4/1989 | Braig | 524/83 |
| 5,152,929 | 10/1992 | Bentley et al. | 252/391 |
| 5,602,196 | 2/1997 | Gilg et al. | 524/171 |

FOREIGN PATENT DOCUMENTS 1042639   9/1966   (GB) .

OTHER PUBLICATIONS

Derwent Abstr. 95–160062/21 for RU 2019558; 1992.
Derwent Abstr. 96–186778/19 for RU 2042709; 1992.

*Primary Examiner*—Robert Gerstl
(74) *Attorney, Agent, or Firm*—Kevin T. Mansfield

(57) ABSTRACT

Suitable lubricant additives are the compounds of formulae

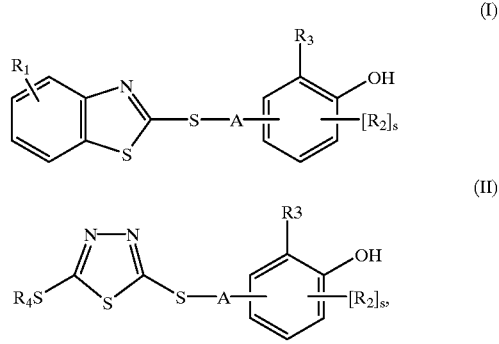

wherein the substituents and groups have the following preferred meanings:

$R_1$=H; $R_2$=methyl or tert-butyl; $R_3$=tert-butyl;
s=0, 1 or 2;
$R_4$=—A—[$(C_6H_2)$(methyl or tert-butyl)(OH)(tert-butyl)];
A=—$CH_2CH_2O$—(C=O)—$CH_2CH_2$— or —$CH_2CH(CH_3)$—O—(C=O)—$CH_2CH_2$—.

7 Claims, No Drawings

PHOSPHORUS-FREE MULTIFUNCTIONAL ADDITIVES FOR LUBRICANTS

The present invention relates to compounds of formula I and II, which are suitable as ash-free antiwear additives and antioxidants, to lubricant compositions comprising said compounds as well as to the use thereof.

For operating combustion engines, it has been found advantageous to use lubricants having a low metal content and, therefore, a low ash content and, in view of exhaust gas catalyst compatibility, also a low phosphorus content. There is therefore a search for metal-free and phosphorus-free additives or additive combinations which approach the good antioxidative and wear protection of the zinc dialkyldithiophosphates. Some experiments are known to intramolecularly combine chemical substructures promising different functions as oil additives.

U.S. Pat. No. 3,676,449 describes 1,3,4-thiadiazole-bridged bis-thiomethylene-phenols of the formula

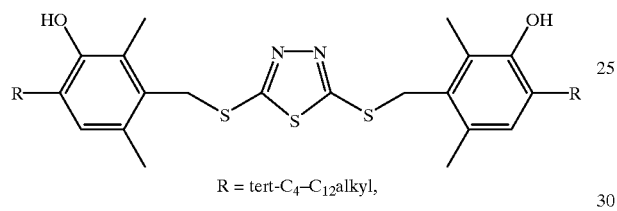

R = tert-$C_4$–$C_{12}$alkyl, which are suitable as antioxidants for materials susceptible to oxidation, in particular polyolefins.

U.S. Pat. No. 4,906,393 describes borates as reaction products of

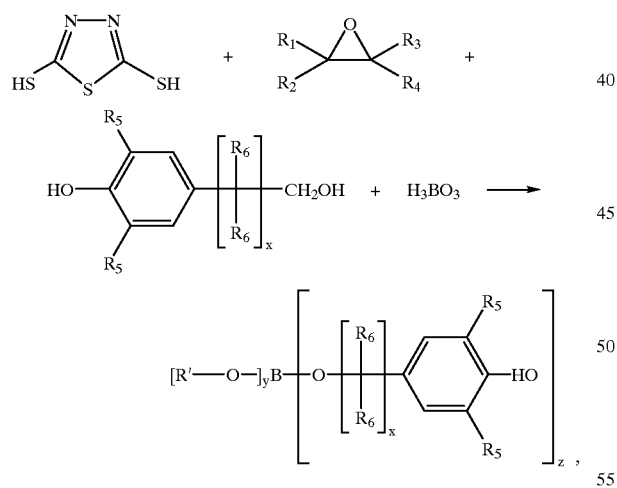

wherein $R_1$, $R_2$, $R_3$ and $R_4$ are hydrogen or $C_1$–$C_{60}$ hydrocarbon, optionally comprising S, N and/or O; $R_5$ and $R_6$ are hydrogen or $C_1$–$C_{20}$hydrocarbon, optionally comprising S, N and/or O; R' is a dimercaptothiadiazole unit; X=0–10, and y+z=3.

U.S. Pat. No. 5,177,212 describes the use of reaction products of 2,5-dimercapto-1,3,4-thiadiazole of type a), b) or c) with aliphatic or aromatic aldehyde and alkylated phenol, at a ratio of 1:1:1 to 2:2:1, as antiwear additives and antioxidants for lubricant compositions:

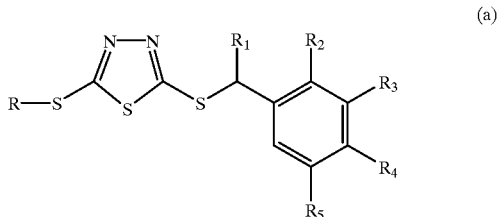

(a)

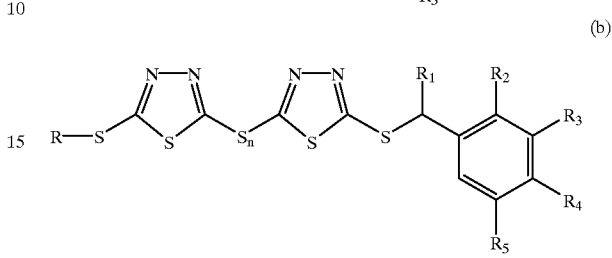

(b)

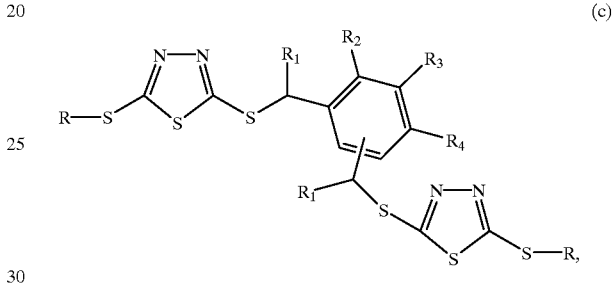

(c)

wherein R=H, the terpene radical, a polymer radical (ex poly-α-olefin or epoxidised poly-α-olefin); $R_1$=H, $C_1$–$C_{17}$alkyl, phenyl, alkyl-substituted phenyl; $R_2$ and $R_4$=H, OH or alkyl, either $R_2$ or $R_4$ being defined as OH; $R_3$ and $R_5$=alkyl, and n=1–2.

This invention relates to compounds of formulae I and II described hereinafter, which are suitable as ash- and phosphorus-free antiwear additives and which additionally have an anti-oxidative effect:

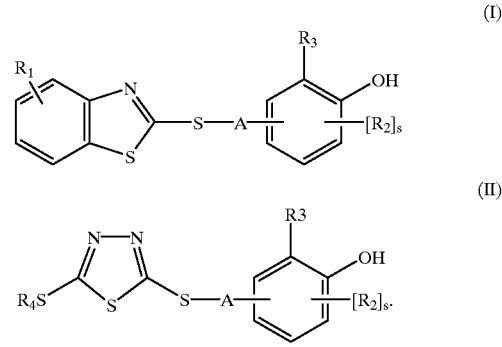

In these formulae:

$R_1$=hydrogen or $C_1$–$C_{20}$alkyl;

$R_2$=hydrogen, $C_1$–$C_{18}$alkyl, $C_5$–$C_{12}$cycloalkyl, $C_7$–$C_{10}$bicycloalkyl, phenyl or $C_7$–$C_9$phenylalkyl;

$R_3$=$C_1$–$C_{18}$alkyl, $C_5$–$C_{12}$cycloalkyl, phenyl or $C_7$–$C_9$phenylalkyl;

s=0, 1 or 2;

$R_4$=$C_5$–$C_{20}$alkyl, $C_5$–$C_{12}$cycloalkyl, phenyl, naphthyl, $C_7$–$C_9$phenylalkyl, which may be interrupted by one or several bivalent radicals from the group consisting of —O—, —NR$_5$—, —S—, —C(=O)—O—, —O—C(=O)—, —C(=O)—NR$_5$— and —NR$_5$—C(=O)— or substituted by one or several radicals from the group consisting of —OH, —NH$_2$ and —C(=O)—OH, or is —A—[(C$_6$H$_2$)R$_2$(OH)R$_3$];

R$_5$=H or C$_1$–C$_{18}$alkyl;

A=C$_1$–C$_{25}$alkylene which may be interrupted by one or several bivalent radicals from the group consisting of —O—, —NR$_5$—, —S—, —C(=O)—O—, —O—C(=O)—, —C(=O)—NR$_5$— and —NR$_5$—C(=O)— or substituted by one or several radicals from the group consisting of —OH, —NH$_2$ and —C(=O)—OH, at least one unit —C(=O)—O— or —O—C(=O)— being present.

It is preferred that:

R$_1$=H;

R$_2$=H, C$_1$–C$_8$alkyl, C$_5$–C$_6$cycloalkyl, phenyl, benzyl or 2-norbornyl;

R$_3$=C$_1$–C$_8$alkyl, C$_5$–C$_6$cycloalkyl, phenyl, benzyl or 2-norbornyl;

s=0, 1 or 2;

R$_4$=C$_5$–C$_7$cycloalkyl, phenyl, benzyl, C$_1$–C$_{18}$alkyl, which may be interrupted by one or several bivalent radicals from the group consisting of —O—, —NH—, —S—, —C(=O)—O—, —O—C(=O)—, —C(=O)—NR$_5$— and —NR$_5$—C(=O)— or substituted by one or several radicals from the group consisting of —OH and —C(=O)—OH, or is —A—[(C$_6$H$_2$)R$_2$(OH)R$_3$];

R$_5$=H or C$_1$–C$_8$alkyl;

A=C$_1$–C$_{18}$alkylene which may be interrupted by one or several bivalent radicals from the group consisting of —O—, —NR$_5$—, —S—, —C(=O)—, —O—C(=O)—, —C(=O)—NR$_5$— and —NR$_5$—C(=O)— or substituted by one or several radicals from the group consisting of —OH, —NH$_2$ and —C(=O)—OH, at least one unit —C(=O)—O— or —O—C(=O)— being present.

It is particularly preferred that:

R$_1$=H; R$_2$=methyl or tert-butyl; R$_3$=tert-butyl;

s=0, 1 or 2;

R$_4$=—A—[(C$_6$H$_2$)(methyl or tert-butyl)(OH)(tert-butyl)];

A=—CH$_2$CH$_2$O—(C=O)—CH$_2$CH$_2$— or —CH$_2$CH(CH$_3$)—O—(C=O)—CH$_2$CH$_2$—.

Very particularly preferred compounds are:

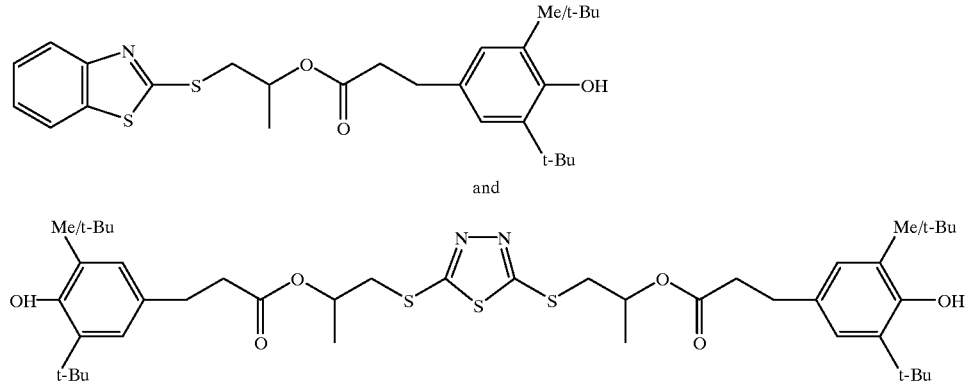

and

These compounds are suitable as multifunctional antiwear additives having additional anti-oxidative activity for base oils of lubricating viscosity as well as for fuels. They are phosphorus-free and substantially ash-free.

In another of its aspects, this invention relates to compositions comprising a compound of formula I or II or mixtures thereof in combination with a base oil of lubricating viscosity or with fuels.

A base oil of lubricating viscosity can be used for the preparation of lubricating greases or lubricants and for metal working, gear or hydraulic fluids.

Such lubricating greases or lubricants, metal working, gear and hydraulic fluids are based, for example, on mineral or synthetic lubricants or oils or on mixtures thereof. The skilled person is familiar with them, and they are described in the relevant literature, for example in *Chemistry and Technology of Lubricants*; Mortier, R. M. and Orszulik, S. T. (Editors); 1992 Blackie and Son Ltd. for GB, VCH-Publishers N.Y for U.S., ISBN 0-216-92921-0, see pages 208 et seq. and 269 et seq.; in *Kirk-Othmer Encyclopedia of Chemical Technology*, fourth Edition 1969, J. Wiley & Sons, New York, Vol. 13, page 533 et seq. (Hydraulic Fluids); *Performance Testing of Hydrauic Fluids*; R. Tourret and E P. Wright, Hyden & Son Ltd. GB, on behalf of The Institute of Petroleum London, ISBN 0 85501 317 6; *Ullmann's Encyclopedia of Ind. Chem.*, Fifth Completely revised Edition, Verlag Chemie, DE-Weinheim, VCH-Publishers for U.S., Vol. A 15, page 423 et seq. (lubricants), Vol. A 13, page 165 et seq. (hydraulic fluids).

This invention also relates to a process for improving the performance properties of lubricants or lubricating greases, such as motor oil, turbine oil, gear oil, hydraulic or metal working fluids or liquid fuels (diesel or carburettor fuels), which comprises adding at least one compound of formula I or II to the base oil or fuel to achieve a friction-reducing and/or antioxidative effect. Accordingly, this invention also relates to the use of compounds of formula I or II as additives in motor oils, turbine oils, gear oils, hydraulic fluids, metal working fluids, lubricating greases or diesel or carburettor fuels.

The lubricants are preferably oils and greases, based e.g. on a mineral oil. Oils are preferred.

Another group of lubricants which may be used are vegetable or animal oils, fats, tallows and waxes or their mixtures with each other or their mixtures with the mentioned mineral or synthetic oils. Vegetable and animal oils, fats, tallows and waxes are, for example, palmnut oil, palm oil, olive oil, beet oil, rapeseed oil, linseed oil, groundnut oil, soybean oil, cottonseed oil, sunflower oil, pumpkin seed oil, coconut oil, corn oil, castor oil, walnut oil and mixtures thereof, fish oils, tallows of slaughter animals, such as beef tallow, neat's foot oil and bone fat as well as their modified epoxidised and sulfoxidised forms, for example epoxidised soybean oil.

Examples of synthetic lubricants include lubricants based on aliphatic or aromatic carboxylates, polymeric esters, polyalkylene oxides, poly-α-olefins or silicones, on a diester of divalent acids with a monovalent alcohol, e.g. dioctyl sebacate or dinonyl adipate, on a triester of trimethylolpropane with a monovalent acid or with a mixture of such acids, e.g. trimethylolpropane tripelargonate, trimethylolpropane tricaprylate or mixtures thereof, on a tetraester of pentaerythritol with a monovalent acid or with a mixture of such acids, e.g. pentaerythritol tetracaprylate, or on a complex ester of monovalent and divalent acids with polyvalent alcohols, for example a complex ester of trimethylolpropane with caprylic and sebacic acid or of a mixture thereof. Particularly suitable are, besides mineral oils, e.g. poly-α-olefins, ester-based lubricants, glycols, polyglycols and polyalkylene glycols and their mixtures with water.

Metal working fluids and hydraulic fluids can be prepared on the basis of the same substances as those described above for the lubricants. They are often also emulsions of such substances with water or other liquids.

The lubricant compositions of this invention are used, for example in combustion engines, e.g. in motor vehicles equipped e.g. with engines of the Otto, diesel, two-stroke, Wankel or orbital type.

The compounds of formula I or II are readily soluble in lubricants, in metal working and hydraulic fluids and are therefore particularly suitable as additives for lubricants, metal working and hydraulic fluids.

The compositions expediently comprise 0.005 up to 10.0% by weight of the compounds of formula I or II, preferably 0.01–5.0% by weight, more preferably 0.01–0.9% weight.

The compounds of formula I or II can be admixed to the lubricants in a manner known per se. The compounds are readily soluble e.g. in oils. They can also be used together with additional additives to prepare a concentrate or a so-called additive packet which, depending on the consumption, can be diluted to the concentrations to be used for the corresponding lubricant.

The compositions of this invention can additionally contain further additives which are added to further improve their basic properties. These additives include: additional antioxidants, metal passivators, rust inhibitors, viscosity index improvers, pour point depressants, dispersants, detergents, other extreme pressure additives, antiwear additives and friction reducers. Where appropriate, these additives can act synergistically with each other or with the novel compounds. Such additives are added in the usual amounts ranging from about 0.01 to 10.0% by weight each. Should it still be necessary to add phophorus- or metal-containing additives, then these additives are preferably added in small amounts, for example of about 0.01 to 0.1% by weight.

Preparation: The compounds of formulae I and II can be prepared by transesterifying or esterifying carboxylate- or carboxylic acid chloride-functionalised alkylphenols with alcohol-functionalised S-alkylmercapto-S/N-heterocycles [e.g. Examples 2, 3, 5, 7, 8, 10, 12, 13] or carboxylate- or carboxylic acid chloride-functionalised S-alkylmercapto-S/N-heterocycles with alcohol-functionalised alkylphenols [e.g. Example 14].

Typical examples of additional additives are the following:

Examples of phenolic antioxidants:

1.1 Alkylated monophenols, for example 2,6-di-tert-butyl-4-methylphenol, 2-tert-butyl-4,6-di-methylphenol, 2,6-di-tert-butyl-4-ethylphenol, 2,6di-tert-butyl-4-n-butylphenol, 2,6di-tert-butyl-4-isobutylphenol, 2,6-dicyclopentyl-4-methylphenol, 2-(1-methylcyclohexyl)-4,6-dimethyl-phenol, 2,6-dioctadecyl-4-methylphenol, 2,4,6-tricyclohexylphenol, 2,6-di-tert-butyl-4-methoxymethylphenol, nonylphenols which are linear or branched in the side chains, for example 2,6-di-nonyl-4-methylphenol, 2,4-dimethyl-6-(1'-methylundec-1'-yl)phenol, 2,4-dimethyl-6-(1'-methylheptadec-1'-yl)phenol, 2,4-dimethyl-6-(1'-methyltridec-1'-yl)phenol and mixtures thereof.

1.2 Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3 Hydroquinones and alkylated hydroquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4 Tocopherols, for example α-, β-, γ- or δ-tocopherol and mixtures thereof (vitamin E).

1.5 Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis(3,6-di-sec-amylphenol), 4,4'-bis(2,6-dimethyl-4-hydroxyphenyl) disulfide.

1.6 Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6(α,α-dimethylbenzyl)-4-nonylphenol], 4,4'-methylenebis-(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1-bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate, 1,1-bis-(3,5-dimethyl-2-hydroxyphenyl)butane, 2,2-bis(3,5-di-tert-butyl-4-hydroxyphenyl)propane, 2,2-bis(5-tert-butyl-4-hydroxy2-methylphenyl)-4-n-dodecylmercaptobutane, 1,1,5,5-tetra(5-tert-butyl-4-hydroxy-2-methylphenyl)pentane.

1.7 O- , N- and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4 -tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8 Hydroxybenzylated malonates, for example dioctadecyl-2,2-bis-(3,5-di-tert-butyl-2-hydroxybenzyl) malonate, di-octadecyl-2(3-tert-butyl-4-hydroxy-5-methylbenzyl)malonate, didodecylmercaptoethyl-2,2-bis(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9 Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10 Triazine compounds, for example 2,4-bis (octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris-(3,5-di-tert-butyl-4-hydroxyphenoxy)-1,2,3-triazine, 1,3,5-tris(3,5-di-tert-butyl-4-hydroxybenzyl)isocyanurate, 1,3,5-tris(4-tert-butyl-3-hydroxy-2,6-dimethylbenzyl) isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl)-isocyanurate.

1.11 Benzylphosphonates, for example dimethyl-2,5-di-tert-butyl-4-hydroxybenzylphosphonate, diethyl-3,5-di-tert-butyl-4-hydroxybenzylphosphonate, dioctadecyl-3,5-di-tert-butyl-4-hydroxybenzylphosphonate, dioctadecyl-5-tert-butyl-4-hydroxy3-methylbenzylphosphonate, the calcium salt of the monoethyl ester of 3,5-di-tert-butyl-4-hydroxybenzylphosphonic acid.

1.12 Acylaminophenols, for example 4-hydroxylauranilide, 4-hydroxystearanilide, octyl N-(3,5-di-tert-butyl-4-hydroxyphenyl)carbamate.

1.13 Esters of β-(3,5-di-tert-butyl-4-hydroxyphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.14 Esters of β-(5-tert-butyl-4-hydroxy-3-methylphenyl) propionic acid with mono- or polyhydric alcohols, e.g. with methanol, ethanol, n-octanol, i-octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris (hydroxyethyl) isocyanurate, N,N'-bis-(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.15 Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.16 Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl)oxamide, 3-thiaundecanol, 3-thiapentadecanol, trimethylhexanediol, trimethylolpropane, 4-hydroxymethyl-1-phospha-2,6,7-trioxabicyclo[2.2.2]octane.

1.17 Amides of β-(3,5-di-tert-butyl-4-hydroxyphenyl) propionic acid e.g. N,N'-bis(3,5-di-tert-butyl-4-hydroxyphenylpropionyl)hexamethylenediamine, N,N'-bis (3,5-di-tert-butyl-4-hydroxyphenylpropionyl) trimethylenediamine, N,N'-bis(3,5-di-tert-butyl-4-hydroxyphenylpropionyl)-hydrazine.

1.18. Ascorbic acid (vitamin C)

1.19. Aminic antioxidants: for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)-p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3-dimethylbutyl)-N'-phenyl-p-phenylenediamine, N-(1-methylheptyl)-N'-phenyl-p-phenylenediamine, N-cyclohexyl-N'-phenyl-p-phenylenediamine, 4-(p-toluenesulfamoyl)diphenylamine, N,N'-dimethyl-N,N'-di-sec-butyl-p-phenylenediamine, diphenylamine, N-allyldiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyldiphenylamine, 4-n-butylaminophenol, 4-butyrylaminophenol, 4-nonanoylamino-phenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino) propane, (o-tolyl)biguanide, bis[4-(1', 3'-dimethylbutyl) phenyl]amine, tert-octylated N-phenyl-1-naphthylamine, a mixture of mono- and dialkylated tert-butyl/tert-octyl-diphenylamines, a mixture of mono- and dialkylated nonyldiphenylamines, a mixture of mono- and dialkylated dodecyldiphenylamines, a mixture of mono- and dialkylated isopropyl/isohexyldiphenylamines, a mixture of mono- and dialkylated tert-butyldiphenylamines, 2,3-dihydro-3,3-dimethyl-4H-1,4-benzothiazine, phenothiazine, a mixture of mono- and dialkylated tert-butyl/tert-octylphenothiazines, a mixture of mono- and dialkylated tert-octyl-phenothiazines, N-allylphenothiazine, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

Examples of other antioxidants:

Aliphatic or aromatic phosphites, esters of thiodipropionic acid or of thiodiacetic acid, or salts of dithiocarbamic or dithiophosphoric acid, 2,2,12,12-tetramethyl-5,9-dihydroxy-3,7,11-trithiatridecane and 2,2,15,15-tetramethyl-5,12-dihydroxy-3,7,10,14-tetrathiahexadecane.

Examples of metal deactivators, for example for copper, are:

a) Benzotriazoles and the derivatives thereof, for example 2-mercaptobenzotriazole, 2,5-dimercaptobenzotriazole, 4- or 5-alkylbenzotriazoles (e.g. tolutriazole) and the derivatives thereof, 4,5,6,7-tetrahydrobenzotriazole and 5,5'-methylenebisbenzotriazole; Mannich bases of benzotriazole or tolutriazole, e.g. 1-[bis(2-ethylhexyl)aminomethyl] tolutriazole and 1-[bis(2-ethylhexyl)aminomethyl] benzotriazole; and alkoxyalkylbenzotriazoles such as 1-(nonyloxymethyl)benzotriazole, 1-(1-butoxyethyl) benzotriazole and 1-(1-cyclohexyloxybutyl)tolutriazole.

b) 1,2,4-Triazoles and the derivatives thereof, for example 3-alkyl(or aryl)-1,2,4-triazoles, and Mannich bases of 1,2, 4-triazoles, such as 1-[bis(2-ethylhexyl)aminomethyl-1,2,4-triazole; alkoxyalkyl-1,2,4-triazoles such as 1-(1-butoxyethyl)-1,2,4-triazole; and acylated 3-amino-1,2,4-triazoles.

c) Imidazole derivatives, for example 4,4'-methylenebis (2-undecyl-5-methylimidazole) and bis[(N-methyl) imidazol-2-yl]carbinol octyl ether.

d) Sulfur-containing heterocyclic compounds, for example 2-mercaptobenzothiazole, 2,5-dimercapto-1,3,4-thiadiazole and derivatives thereof; and 3,5-bis[di(2-ethylhexyl)aminomethyl]-1,3,4-thiadiazolin-2-one.

e) Amino compounds, for example salicylidenepropylenediamine, salicylaminoguanidine and the salts thereof.

Examples of rust inhibitors are:

a) Organic acids, their esters, metal salts, amine salts and anhydrides, for example alkyl- and alkenylsuccinic acids and their partial esters with alcohols, diols or hydroxycarboxylic acids, partial amides of alkyl- and alkenylsuccinic acids, 4-nonylphenoxyacetic acid, alkoxy- and alkoxyethoxycarboxylic acids such as dodecyloxyacetic acid, dodecyloxy(ethoxy)acetic acid and the amine salts thereof, and also N-oleoylsarcosine, sorbitan monooleate, lead naphthenate, alkenylsuccinic anhydrides, for example dodecenylsuccinic anhydride, 2-(2-carboxyethyl)-1-dodecyl-3-methylglycerol and the salts thereof, in particular the sodium salts and triethanolamine salts.

b) Nitrogen-containing compounds, for example:
i. Primary, secondary or tertiary aliphatic or cydoaliphatic amines and amine salts of organic and inorganic acids, for example oil-soluble alkylammonium carboxylates, and also 1-[N,N-bis(2-hydroxyethyl)amino]-3-(4-nonylphenoxy)propan-2-ol.
ii. Heterocyclic compounds, for example: substituted imidazolines and oxazolines, and 2-heptadecenyl-1-(2-hydroxyethyl)imidazoline.

c) Phosphorus-containing compounds, for example: Amine salts of phosphoric acid partial esters or phosphonic acid partial esters, and zinc dialkyldithiophosphates.

d) Sulfur-containing compounds, for example: barium dinonylnaphthalenesulfonates, calcium petroleum sulfonates, alkylthio-substituted aliphatic carboxylic acids, esters of aliphatic 2-sulfocarboxylic acids and the salts thereof.

e) Glycerol derivatives, for example: glycerol monooleate, 1-(alkylphenoxy)-3-(2-hydroxy-ethyl)glycerol, 1-(alkylphenoxy)-3-(2,3dihydroxypropyl)glycerol and 2-carboxyalkyl-1,3-dialkylglycerol.

Examples of viscosity index improvers are:
Polyacrylates, polymethacrylates, vinylpyrrolidone/methacrylate copolymers, polyvinylpyrrolidones, polybutenes, olefin copolymers, styrene/acrylate copolymers and polyethers.

Examples of pour-point depressants are:
Poly(meth)acrylates, ethylene/vinyl acetate copolymer, alkyl polystyrenes, fumarate copolymers, alkylated naphthalene derivatives.

Examples of dispersants/surfactants are:
Polybutenylsuccinic amides or -imides, polybutenylphosphonic acid derivatives and basic magnesium, calcium and barium sulfonates and basic magnesium, calcium and barium phenolates.

Examples of extreme pressure and antiwear additives are:
Sulfur- and/or phosphorus- and/or halogen-containing compounds, for example chlorinated paraffins, sulfurised olefins or vegetable oils (soybean oil and rapeseed oil), alkyl- or aryl-di- or -trisulfides, zinc dialkyldithiophosphates, such as zinc-bis(2-ethylhexyl) dithiophosphate, zinc dithiocarbamates, such as zinc diamyldithiocarbamate, molybdenum phosphorodithioates, molybdenum dithiocarbamates, triarylphosphates, such as tritolylphosphate, tricresylphosphate, isopropyl phenylphosphate, amine salts of mono- or dialkylphosphoric acids, e.g. the amine salts of mono/di-hexylphosphate, amine salts of alkylphosphonic acids, such as the amine salt of methylphosphonic acid, triaryl phosphites, e.g. tris [nonylphenyl]phosphite, dialkyl phosphites, such as dioctyl phosphite, triaryl monothiophosphates, e.g. triphenyl thionophosphate or tris-[isononylphenyl]thionophosphate or tert-butylated triphenyl thionophosphates, substituted trialkyl mono- or dithiophosphates, for example [(diisopropoxyphosphinothioyl)thio]propionate or butylene-1,3bis[(diisobutoxyphosphinothioyl)propionate], trithiophosphates, such as trithiophosphoric acid, S,S,S-tris (isooctyl-2-acetate), amine salts of 3-hydroxy-1,3-thiaphosphetane-3-oxide, benzotriazoles or the derivatives thereof, e.g. bis(2-ethylhexyl)aminomethyltolutriazole, dithiocarbamates, such as methylene-bis-dibutyldithiocarbamate, derivatives of 2-mercaptobenzothiazole, e.g. 1-[N,N-bis(2-ethylhexyl) aminomethyl]-2-mercapto-1H-1,3-benzothiazole, derivatives of 2,5-dimercapto-1,3,4-thiadiazole, such as 2,5-bis (tert-nonylditdithio)-1,3,4-thiadiazole.

Examples of frictional coefficient reducers are, for example, lard oil, oleic acid, tallow, rapeseed oil, sulfurised fats, amines. Other examples are cited in EP-A-565487.

Examples of special additives for use in water/oil metal working and hydraulic fluids are:
Emulsifiers: petroleum sulfonates, amines, such as polyethoxylated fatty amines, nonionic surface active substances; buffers: alkanolamines; biocides: triazines, thiazolinones, trisnitromethane, mopholine, sodium pyridene ethol; processing speed improvers: calcium sulfonates and barium sulfonates;

Examples of fuel additives:
Such additives are described in Kirk-Othmer, *Encyclopedia of Chemical Technology*, Vol. 12, 1994. They are mainly gasoline and diesel additives:

Gasoline: aminic antioxidants, in particular para-phenylenediamines, or phenolic antioxidants, e.g. 2,6-di-tert-butylphenol (as described above); metal deactivators, in particular N,N'-disalicylidene-1,2-propane, benzotriazole, EDTA; rust inhibitors, for example carboxylic acids, sulfonates, amines or amine salts; dispersants, e.g. esters, amines of high molecular weight, Mannich bases, succinimides, boronated succinimides; detergents, for example fatty acid amides, non-polymeric amines, polybutene succinimides, polyether amines, low molecular weight amines, sulfonates, salicylic acid derivatives; demulsifiers, for example long-chain alcohols or phenols containing polyethylene or polybutylene groups; antiknock additives, for example manganese methylcyclopentadienyltricarbonyl, oxygen compounds, e.g. esters of vegetable oils, ethers, alcohols for improving the burning behaviour.

Diesel fuels: ignition improvers (cetane improvers), e.g. alkyl nitrates, ether nitrates, alkyl diglycol nitrates, organic peroxides; stabilisers, in particular for cracked diesel: amines and other N-containing compounds which act as radical interceptors; rust inhibitors, as described above;

detergents as described above; oxygen compounds as described above; cold flow improvers, i.e. for example pour point depressants (see above), cloud point depressants or so-called operability additives (OA), which are polymeric multicomponent systems improving, inter alia, the filter flow behaviour.

The starting products are known per se and/or their preparation is described in the following Examples [e.g. Examples 1, 4, 6, 9, 11].

EXAMPLES

This invention is illustrated by the following Examples. Parts or percentages are by weight, unless otherwise stated.

Example 1

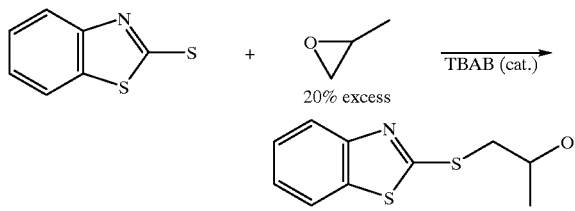

70 g (1.2 mol) of propylene oxide are added dropwise over 30 min at 35° C. to a suspension consisting of 172 g (1 mol) of 2-mercaptobenzothiazole and 16.1 g (50 mmol) of tetrabutylammonium bromide in 900 ml of toluene, and the reaction is allowed to go to completion over 4 hours at 40° C. This mixture is then extracted twice with about 100 ml of 2N NaOH solution and washed with 5×100 ml of water (→pH 7–8). The organic phase is concentrated by evaporation and dried at reduced pressure (80° C./about 0.03 mbar), giving 227 g of a clear, pale brown oil of medium viscosity (about 100% of theory) [75235-71-1].

Elemental analysis: 53.36% C (calculated 53.31); 4.92% H (calculated 4.92); 6.09% N (calculated 6.22); 28.56% S (calculated 28.46).

Example 2

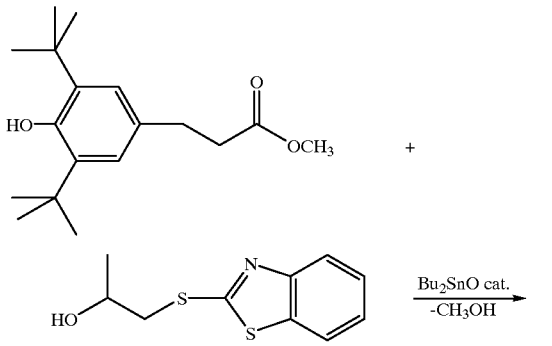

-continued

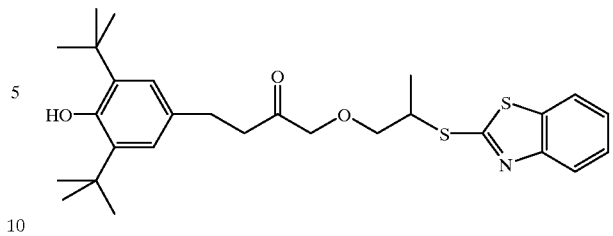

166 g (0.7 mol) of the product of Example 1 [75235-71-1], dissolved in 100 ml of toluene, are added dropwise over 2 hours at 135–140° C. to a melt consisting of 204.7 g (0.7 mol) of Metilox® (Ciba Specialty Chemicals) *) and 8.7 g (35 mmol) of dibutyltin oxide, distilling off toluene and methanol at the same time. After the addition is complete, the mixture is allowed to react for 4 hours at 135–140° C., while a total of about 50 ml of toluene is added dropwise and distilled off at the same time. After adding another 3.5 g (14 mmol) of dibutyltin oxide, the reaction is allowed to go to completion over another 4 hours at 135–140° C. (+toluene, −toluene/methanol).—Unreacted METILOX (about 103 g, 0.35 mol) is removed by distillation at reduced pressure (140° C./about 0.03 mbar). The remaining yellow oil of medium viscosity is dissolved in about 400 ml of special-boiling point spirit (b.p. 80–10° C.), extracted twice with about 100 ml of 2N NaOH solution and washed with 3×c. 100 ml of water (→pH 7). The organic phase is clarified by fiftration through a small amount of filter aid (Hyflo®), concentrated by evaporation and dried at reduced pressure (140° C./c. 0.03 mbar), giving 224 g of a viscous, pale orange and clear oil (66% of theory).

Elemental analysis: 64.75% C (calculated 66.77); 7.42% H (calculated 7.26); 3.22% N (calculated 2.88); 14.26% S (calculated 13.20).

*) methyl β-(3.5-di-tert-butyl-4-hydroxyphenyl) propionate [6386-38-5].

Example 3

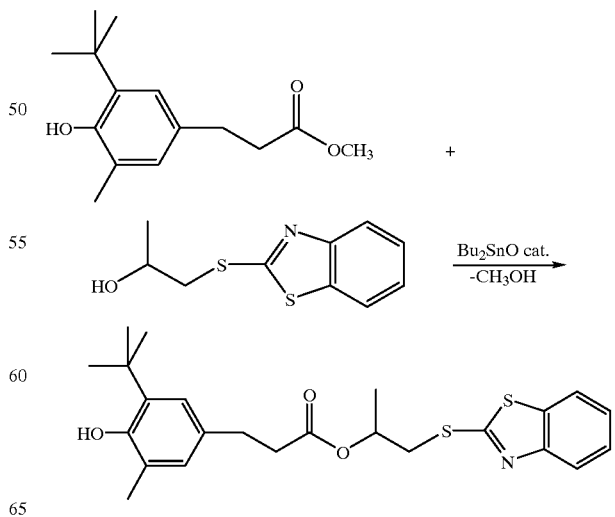

In the same manner as in Example 2, 22.15 g (90 mmol) of methyl-METILOX *) are reacted with 20.3 g (90 mmol) of the product of Example 1 [75235-71-1] in the presence of a catalytic amount of dibutyltin oxide (1.12 g+0.6 g, 6.9 mmol), giving 27.9 g of a brown oil of high viscosity (70% of theory).

Elemental analysis: 64.51% C (calculated 64.83); 6.76% H (calculated 6.80); 3.2% N (calculated 3.15); 14.06% S (calculated 14.42).

*) methyl β-(5-tert-butyl-4hydroxy-3-methylphenyl) propionate [6386-39-6].

Example 4

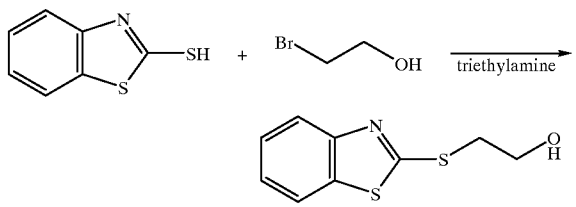

125 g (1.0 mol) of 2-bromoethanol are added dropwise over 1.5 hours at 30–40° C. to an emulsion consisting of 172 g (1.0 mol) of 2-mercaptobenzothiazole and 121.4 g (1.2 mol) of triethylamine in 1 l of toluene. This mixture is then stirred for 1.5 hours at 30° C. and for 2.5 hours at 70 C. The fine suspension is washed with 2×500 ml of water, 200 ml of 2N NaOH solution and again with water (pH 7). Concentration by evaporation and drying at reduced pressure (100° C./c. 0.03 mbar) gives 192 g of a brown oil (91% of theory). This crude product [4665-63-8] is then further reacted directly (e.g. in Example 5).

Example 5

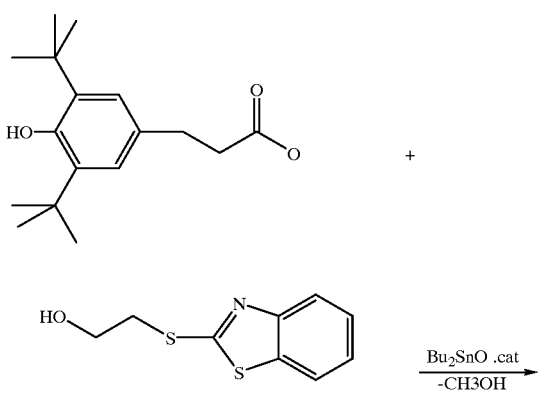

-continued

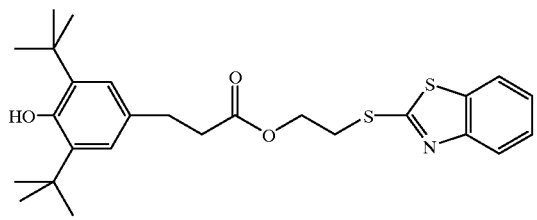

In the same manner as in Examples 2 and 3, 26.3 g (90 mmol) of METILOX are reacted with 19 g (90 mmol) of the product of Example 1 in the presence of a catalytic amount of dibutyltin oxide (1.7 g, 7 mmol). The crude product is preliminarily purified by chromatography over 200 g of silica gel (toluene/ethyl acetate) and is recrystallised from ethanol (c. 190 ml), giving 22 g of a white crystalline product; m.p. 108–111° C. (52% of theory).

Elemental analysis: 66.00% C (calculated 66.21); 7.29% H (calculated 7.05); 2.94% N (calculated 2.97); 13.59% S (calculated 13.59).

Example 6

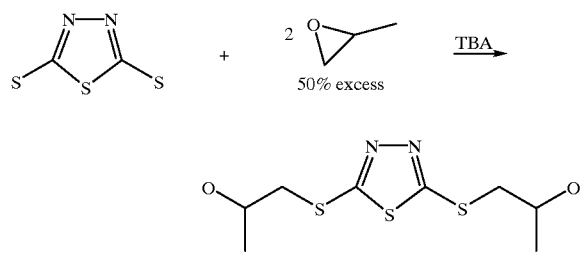

A solution of 76.7 g (1.32 mol) of propylene oxide in 50 ml of tetrahydrofuran is added dropwise over 1 hour at 30–35° C. to a suspension consisting of 66 g (0.44 mol) of 2,5-dimercapto-1,3,4-thiadiazole [1072-71-5] and 7.1 g (22 mmol) of tetrabutylammonium bromide (TBAB) in 270 ml of tetrahydrofuran. The reaction is then allowed to go to completion over 1 hour at 40° C. The dark solution is concentrated by evaporation and the dark oil (c. 130 g) is eluted by chromatography over 500 g of silica gel (toluene/ ethyl acetate). The fractions of the main product are concentrated by evaporation and dried at reduced pressure (120° C./c. 0.03 mbar), giving 97.0 g of an orange viscous oil (83% of theory) [107641-99-6].

Elemental analysis: 36.50% C (calculated 36.07), 5.34% H (calculated 5.30); 10.58% N (calculated 10.52), 36.52% S (calculated 36.10).

Example 7

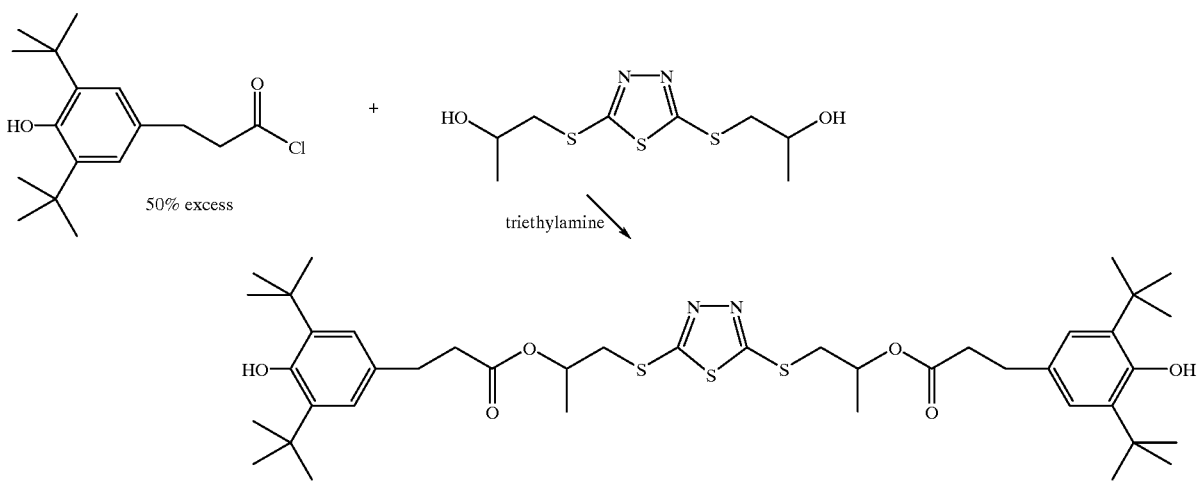

About 25 ml (180 mmol) of triethylamine are added dropwise over 25 min at 5–10° C. to a solution of 16 g (60 mmol) of the product of Example 6 [107641-99-6] and c. 53 g (180 mmol) of METILOX-acid chloride *) in 240 ml of toluene, and the reaction is allowed to go to completion over 4.5 hours at 30–40° C. The turbid orange reaction mixture is washed with 500 ml of water, then with 100 ml of 2N NaOH solution and again with water (→pH 7–8) and is then concentrated by evaporation. The crude product (c. 70 g) is purified by column chromatography over 500 g of silica gel (hexane/toluene/ethyl acetate). The fractions of the main product are concentrated by evaporation and dried at reduced pressure (120° C./c. 0.03 mbar), giving 17.8 g of a yellow tacky resin (38% of theory).

Elemental analysis: 64.42% C (calculated 64.09); 8.06% H (calculated 7.94); 3.47% N (calculated 3.56); 11.74% S (calculated 12.22).

*) β-(3,5-di-tert-butyl-4-hydroxyphenyl)propionic acid chloride [3062-64-4].

The tert-butyl/methyl analogue to Example 7 is obtained in a manner analogous to that of Examples 2, 3 and 5 by catalysed transesterification of 2 equivalents of methyl-METILOX *) with the product of Example 6. This gives 8.0 g of a brown tacky resin (c. 20% of theory).

Elemental analysis: 61.04% C (calculated 61.51); 7.45% H (calculated 7.17); 3.94% N (calculated 3.99); 13.48% S (calculated 13.68).

*) methyl β-(5-tert-butyl-4-hydroxy-3-methylphenyl) propionate [6386-39-6].

Example 9

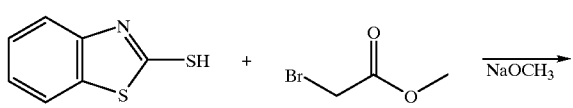

Example 8

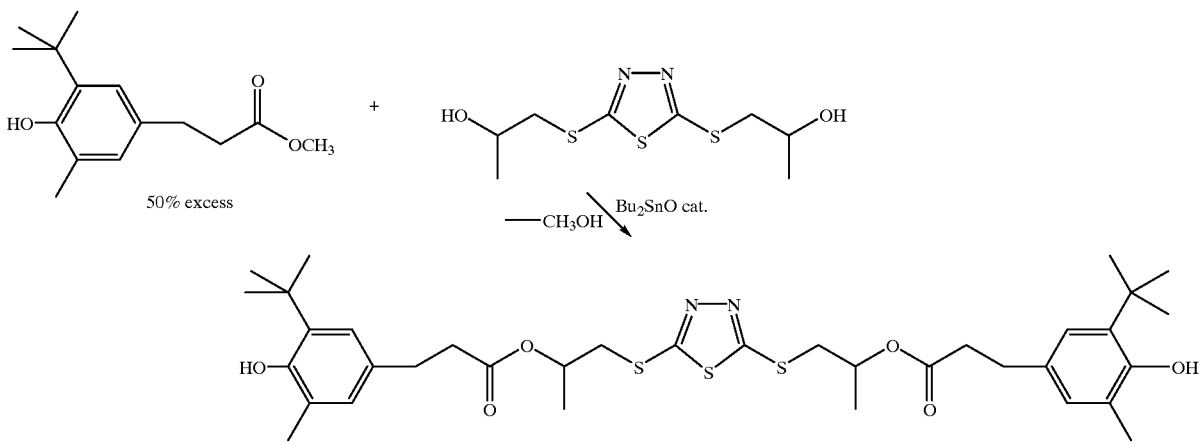

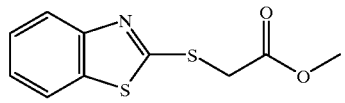

94.6 g (0.6 mol) of methyl bromoacetate are added dropwise over 1 hour at 0–5° C. to a solution of 88 g (0.5 mol) of 2-mercaptobenzothiazole and 108 g of sodium methanolate 30% (0.6 mol) in 850 ml of methanol. This mixture is stirred at room temperature for 1 hour. After concentrating the mixture by evaporation and dissolving it again in 400 ml of toluene, it is washed with 3×100 ml of unsaturated sodium chloride solution until neutral (pH c. 6). The toluene phase is concentrated by evaporation, giving 131 g of a pale orange oil. This crude product is recrystallised from hexane (c. 1200 ml), giving 102 g of a white crystalline product; m.p. 74–76° C. (86% of theory) [24044-87-9].

The product is further reacted in this quality (e.g. in Example 14).

In the same manner as in Examples 2, 3, 5 and 8, 29.4 g (90 mmol) of methyl 3,5-bis(tert-butyl)-4-hydroxybenzylthioacetate [51511-20-7] are reacted with 16.9 g (80 mmol) of the product of Example 1[4665-63-8] in the presence of a catalytic amount of dibutyltin oxide (0.5 g, 9 mmol). The crude product is purified twice by chromatography over 550 g and 300 g, respectively, of silica gel (hexane—toluene—ethyl acetate), giving 8.8 g of a yellow oil of high viscosity (22% of theory).

Elemental analysis: 62.48% C (calculated 61.99); 7.01% H (calculated 6.60); 2.75% N (calculated 2.78); 19.02% S (calculated 19.09).

Example 10

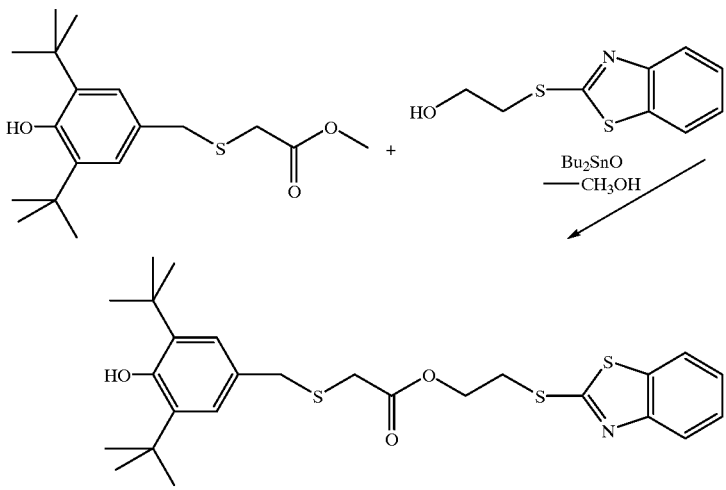

Example 11

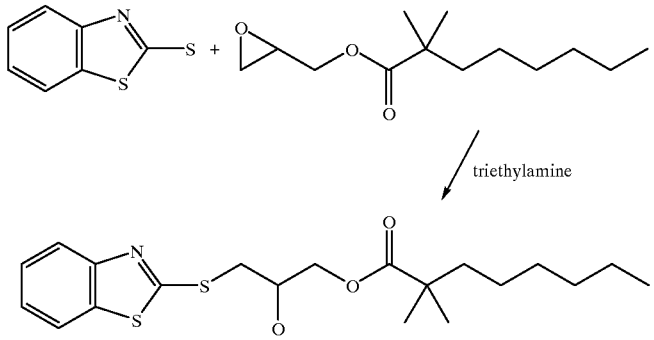

253 g (1.0 mol) of Glydexx® (Exxon) N 10 [Exxon Chemicals: 52636-92-7] are added dropwise over 30 min at 60° C. to a suspension consisting of 172 g (1.0 mol) of 2-mercaptobenzothiazole and 5 ml of triethylamine in 1.5 l of toluene. This mixture is then heated over 15 min to 80° C. and is stirred for 3 hours at this temperature. The toluene solution is then washed with 2×50 ml of 1N NaOH solution and with 4×50ml of water until neutral (pH 7). The organic phase is clarified by filtration through a small amount of filter aid (HYFLO). Concentration by evaporation and drying at reduced pressure (100° C./c. 0.03 mbar) gives 405 g (c. 100% of theory) of a clear oil of medium viscosity; $n_D^{20}$:1.5578.

Elemental analysis: 60.95% C (calculated 60.73); 7.63% H (calculated 7.39); 3.53% N (calculated 3.54); 15.80% S (calculated 16.21).

Example 12

6.7 g (66 mmol) of triethylamine are added dropwise over 15 min at 0–10° C. to a solution of 23.7 g (60 mmol) of the product of Example 11 and 18.7 g (63 mmol) of METILOX acid chloride [3062-64-4] in 200 ml of toluene. This mixture is stirred at room temperature for 3 hours. The brown suspension is then filtered and the filtrate is washed with 1×100 ml of 2N sodium hydroxide solution and water until neutral and is then concentrated by evaporation. The crude product (c. 45 g) is purified by chromatography over 500 g of silica gel (hexane/toluene/ethyl acetate). The fractions with the main product are concentrated by evaporation and dried at reduced pressure (100° C./c.0.03 mbar), giving 21 g of an orange oil of high viscosity (53% of theory).

Elemental analysis: 67.99% C (calculated 67.75); 8.30% H (calculated 8.14); 2.07% N (calculated 2.14); 8.75% S (calculated 9.78).

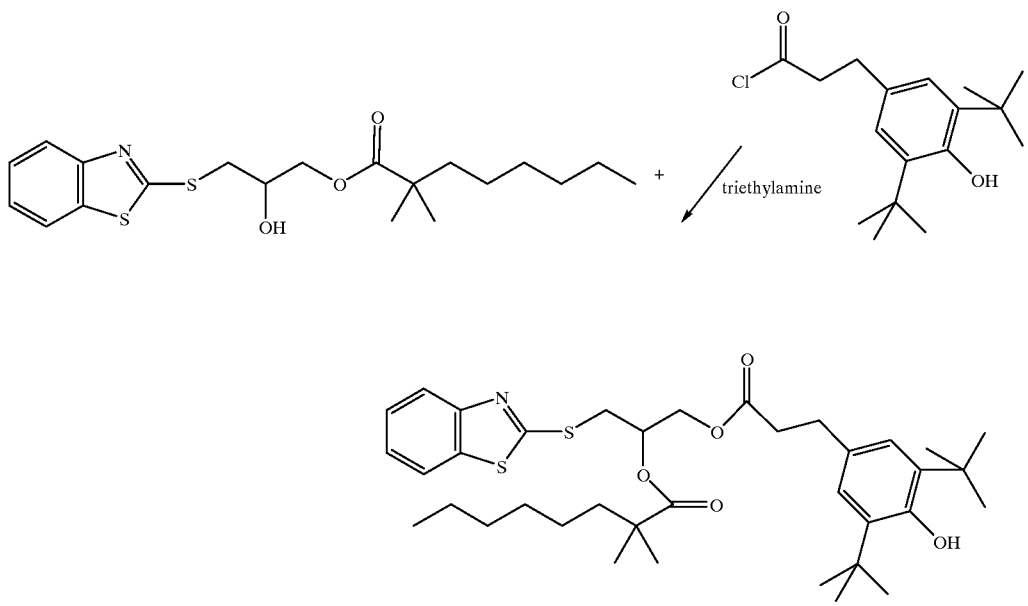

Example 13

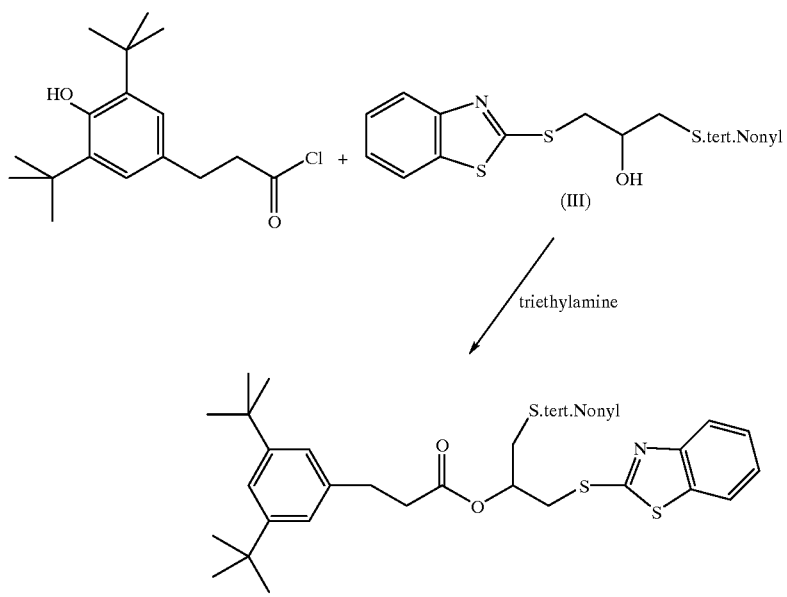

11.1 g (0.11 mol) of triethylamine are added dropwise over 25 min at 0–10° C. to a solution of 38.4 g (0.1 mol) of III *) and 31.2 g (0.105 mol) of METILOX acid chloride [3062-64-4] in 200 ml of toluene, and the reaction is then allowed to go to completion over 2 hours at 30° C. This mixture is diluted at room temperature with 100 ml of hexane and is then filtered and concentrated by evaporation. The crude product (a brown oil, c. 72 g) is purified by column chromatography over about 500 ml of silica gel (hexane/toluene/ethyl acetate). The fractions of the main product are concentrated by evaporation and dried at reduced pressure (100° C./c. 0.03 mbar), giving 46.2 g of a highly viscous oil (72% of theory).

Elemental analysis: 66.7% C (calculated 67.14); 8.49% H (calculated 8.30); 2.28% N (calculated 2.17); 15.03% S (calculated 14.93).

*) see EP 166 696, Ex.13 (using tert-dodecyl)

Example 14

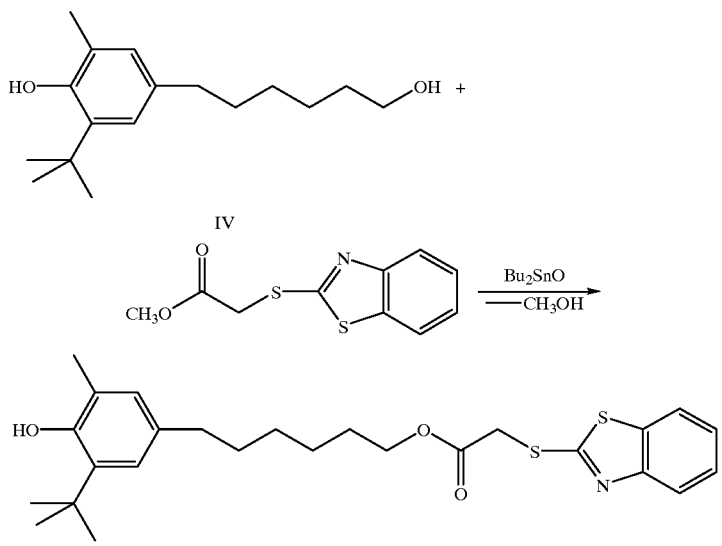

A suspension consisting of 23.8 g (90 mmol) of IV *), 21.5 g (90 mmol) of the product of Example 9 **) and 1.7 g of dibutyltin oxide in 50 ml of toluene is slowly heated to 135–140° C., distilling off the toluene at the same time. Toluene is then continuously added dropwise at this temperature and is removed by distillation together with the released methanol. Another 1.7 g of dibutyltin oxide are added after about 4 hours and then again after 5 hours. After 8 hours, the mixture is concentrated by evaporation and purified by column chromatography over 500 g of silica gel (toluene/ethyl acetate). The fractions of the main product are concentrated by evaporation and dried at reduced pressure (100° C./c. 0.03 mbar, c. 30 min), giving 9.4 g of a highly viscous yellow oil (22% of theory).

Elemental analysis: 66.53% C (calculated 66.21); 7.29% H (calculated 7.05); 2.95% N (calculated 2.97); 13.71% S (calculated 13.59).

*) [152211-02-4]; **)[24044-87-9].

Example 15

Antiwear test: To test the suitability as antiwear additive, the ASTM standard method D-2783-81 is applied using a Shell four-ball tester. The base oil used is Stock 305, of Mobil, to which the compound according to the respective Example cited is added in the amount indicated in Table I. The average wear scar diameter WSD (in mm) is determined at a 40 kg load and at 1440 rpm after 1 hour of operation at 100° C. The results obtained are compiled in Table I.

TABLE I

| Compound of Example | Additive amount [% by weight] | WSD [mm] |
|---|---|---|
| base oil | — | 2.32 |
| 2 | 1.0 | 0.68 |
| 3 | 1.0 | 0.77 |
| 5 | 1.0 | 0.77 |
| 7 | 1.0 | 0.74 |
| 8 | 1.0 | 0.64 |
| 13 | 1.0 | 0.75 |
| 14 | 1.0 | 0.76 |

What is claimed is:

1. A compound of the formula (II)

[structure: $R_4S$—[1,3,4-thiadiazole]—$S$—$A$—[phenyl with $R_3$, OH, $[R_2]_s$]]

wherein
$R_2$=hydrogen, $C_1$–$C_{18}$alkyl, $C_5$–$C_{12}$cycloalkyl, $C_7$–$C_{10}$bicycloalkyl, phenyl or $C_7$–$C_9$phenylalkyl;
$R_3$=$C_1$–$C_{18}$alkyl, $C_5$–$C_{12}$cycloalkyl, phenyl or $C_7$–$C_9$phenylalkyl;
s=0, 1 or 2;
$R_4$=$C_5$–$C_{20}$alkyl, $C_5$–$C_{12}$cycloalkyl, phenyl, naphthyl, $C_7$–$C_9$phenylalkyl, which may be interrupted by one or several bivalent radicals selected from the group consisting of —O—, —$NR_5$—, —S—, —C(=O)—O—, —O—C(=O)—, —C(=O)—$NR_5$— and —$NR_5$—C(=O)— or substituted by one or several radicals selected from the group consisting of —OH, —$NH_2$ and —C(=O)OH, or is —A—(($C_6H_2$)$R_2$(OH)$R_3$);
$R_5$=H or $C_1$–$C_{18}$alkyl;
A=$C_1$–$C_{25}$alkylene which may be interrupted by one or several bivalent radicals selected from the group consisting of —O—, —$NR_5$—, —S—, —C(=O)—O—, —O—C(=O)—, —C(=O)—$NR_5$— and —$NR_5$—C(=O)— or substituted by one or several radicals selected from the group consisting of —OH, —$NH_2$ and —C(=O)—OH, at least one unit —C(=O)—O— or —O—C(=O)— being present.

2. A compound according to claim 1, wherein
$R_2$=methyl or tert-butyl; $R_3$=tert-butyl;
$R_4$=—A—(($C_6H_2$)(methyl or tert-butyl)(OH)(tert-butyl)); and
A=—$CH_2CH_2$O—(C=O)—$CH_2CH_2$— or —$CH_2$CH($CH_3$)—O—(C=O)—$CH_2CH_2$—.

3. A compound according to claim 1, wherein
$R_2$=H, $C_1$–$C_8$alkyl, $C_5$–$C_6$cycloalkyl, phenyl, benzyl or 2-norbornyl;
$R_3$=$C_1$–$C_8$alkyl, $C_5$–$C_6$cycloalkyl, phenyl, benzyl or 2-norbornyl;
$R_4$=$C_5$–$C_7$cycloalkyl, phenyl, benzyl, $C_1$–$C_{18}$alkyl, which may be interrupted by one or several bivalent radicals from the group consisting of —O—, —NH—, —S—, —C(=O)—O—, —O—C(=O)—, —C(=O)—$NR_5$— and —$NR_5$—C(=O)— or substituted by one or several radicals from the group consisting of —OH and —C(=O)—OH, or is —A—[($C_6H_2$)$R_2$(OH)$R_3$] $R_5$=H or $C_1$–$C_8$alkyl;
A=$C_1$–$C_{18}$alkylene which may be interrupted by one or several bivalent radicals from the group consisting of —O—, —$NR_5$—, —S—, —C(=O)—O—, —O—C(=O)—, —C(=O)—$NR_5$— and —$NR_5$—C(=O)— or substituted by one or several radicals from the group consisting of —OH, —$NH_2$ and —C(=O)—OH, at least one unit —C(=O)—O— or —O—C(=O)— being present.

4. Compounds of formulae:

[two chemical structures showing bis-hindered phenol thiadiazole disulfide compounds]

5. A composition, which comprises a compound of formula II according to claim 1 in combination with a base oil of lubricating viscosity or with fuels.

6. A concentrate, which comprises an oil and at least one compound according to claim 1.

7. A process for improving the performance properties of lubricants, lubricating greases or liquid fuels, which comprises adding at least one compound of formula II according to claim 1 thereto.

* * * * *